United States Patent [19]

DeMarco et al.

[11] Patent Number: 4,507,278
[45] Date of Patent: Mar. 26, 1985

[54] LOW AMMONIA BLEACH COMPOSITIONS

[75] Inventors: Richard DeMarco, Danbury, Conn.; John A. Ferguson, Cincinnati, Ohio

[73] Assignee: Clairol Incorporated, New York, N.Y.

[21] Appl. No.: 389,522

[22] Filed: Jun. 17, 1982

Related U.S. Application Data

[63] Continuation of Ser. No. 112,036, Jan. 14, 1980, abandoned, which is a continuation-in-part of Ser. No. 950,922, Oct. 12, 1978, abandoned.

[51] Int. Cl.³ .................. A61K 7/135; A61K 7/06
[52] U.S. Cl. ...................................... 424/62; 424/70
[58] Field of Search ............................. 424/70, 62

[56] References Cited

U.S. PATENT DOCUMENTS

| | | | |
|---|---|---|---|
| 2,283,350 | 5/1942 | Baum | 424/62 |
| 2,991,228 | 7/1961 | Lustig | 424/62 |
| 3,193,464 | 7/1965 | Edman et al. | 424/62 |
| 3,378,444 | 4/1968 | Swanson | 424/62 |
| 3,651,209 | 3/1972 | Cohen | 424/62 |
| 3,651,931 | 3/1972 | Hsiung | 424/62 |
| 3,726,638 | 4/1973 | Ghilardi et al. | 8/111 |
| 3,811,830 | 5/1974 | DeMarco | 424/71 |
| 3,816,615 | 6/1974 | Zeffren et al. | 424/62 |
| 3,823,231 | 7/1974 | Bucaria | 424/62 |
| 3,961,634 | 6/1976 | Busch | 424/62 |
| 3,975,515 | 8/1976 | Wajaroff et al. | 424/72 |
| 3,986,825 | 10/1976 | Sokol | 8/111 |
| 4,010,872 | 3/1977 | Lozano et al. | 8/111 |
| 4,027,008 | 5/1977 | Sokol | 424/62 |

FOREIGN PATENT DOCUMENTS

| | | | |
|---|---|---|---|
| 466172 | 5/1937 | United Kingdom | 424/62 |

*Primary Examiner*—Dale R. Ore
*Attorney, Agent, or Firm*—Gabriel P. Katona

[57] ABSTRACT

An aqueous alkaline thickened low ammonia hair bleaching composition containing hydrogen peroxide, activator, water-soluble surfactant thickener and water-insoluble surfactant thickener; the ammonium ion concentration of said composition being in the range of from about 0.15% to about 0.55% based on the total weight of the composition and the ratio of water-soluble surfactant thickener to water-insoluble surfactant thickener being in the ratio of about 1.8 to about 7.0.

17 Claims, No Drawings

LOW AMMONIA BLEACH COMPOSITIONS

RELATED CASES

This application is a continuation of application Ser. No. 112,036, filed on Jan. 14, 1980, which is a continuation-in-part of application Ser. No. 950,922 filed Oct. 12, 1978, both abandoned.

This invention relates to hair bleaching compositions and more particularly, to hair bleaching compositions containing very low levels of ammonia as measured by the ammonium ion concentrations.

One of the big disadvantages of the bleaching compositions presently available for bleaching human hair is the fact that the ammonia odor generated by these products during use is very unpleasant. The principal active oxidizing agent in these bleaching compositions are peroxide oxidizing agents that usually take the form of an aqueous hydrogen peroxide solution. Although aqueous hydrogen peroxide solution per se under alkaline conditions is effective in oxidizing the pigments in the human hair and thus, is efficacious as a hair bleaching agent, its action is too slow. As a consequence, in addition to the oxidation of the hair pigments, the action desired, a significant amount of hair damage also results; an effect that is obviously to be minimized.

It is known in the prior art that ammonia is an effective activator for the hair bleaching action of aqueous peroxide solutions which serves to speed up the rate at which the hair pigments are oxidized. It has therefore been customary to use ammonia in bleaching compositions for this purpose. In addition, the adjustment of the pH of the aqueous hydrogen peroxide solutions on the alkaline side is a necessary feature if they are to serve as effective bleaching agents for hair.

Although the pH effect is different from the activator effect of ammonia (since the pH effect can be accomplished with alkaline materials other than ammonia), it has been common practice to use the ammonia both for its activator effect and for its pH effect on the composition. As a consequence, with a few exceptions, essentially all the commercial hair bleaching compositions contain substantial quantities of ammonia which makes their use particularly disagreeable because of the strong ammonia odor that they generate.

Aside from the fact that hair bleaching compositions must be such as to effectively oxidize the hair pigments without unduly damaging the hair, it is essential that when applied to the head these compositions be sufficiently high viscosity so as to remain at the site where the bleaching is desired rather than to run down off the head. For this purpose, it has been customary to add to the hair bleaching a water-insoluble thickening agent. By way of illustration, in U.S. Pat. No. 3,651,209 such materials as calcium carbonate, magnesium carbonate, plaster of Paris, talc, kaolin and bentonite have been suggested for use for this purpose. Similarly, U.S. Pat. No. 3,816,615 suggests the use of sodium metasilicate, various clays and carboxymethyl cellulose as thickeners in hair bleaching compositions.

Furthermore, hair lightening lotions presently in use are additionally known to contain substantial quantities of water-insoluble esters, alcohols, ethoxylates and/or propoxylates to create viscosity. The most common alcohol used is the C18 oleyl derivative. The water insoluble surfactants form gels when the lotion is mixed with aqueous peroxide solutions. The water insoluble gel helps keep the bleach mixture on the hair fibers and prevent it from running or creeping away from the hair shaft. The use of water-insoluble surfactants (see U.S. Pat. No. 2,283,350 for the use of high molecular weight alcohols for this purpose), however, greatly affects the lightening ability of the bleach mixture. To overcome reduced bleaching activity, high levels of ammonia are required. Studies have shown that as the surfactant becomes more water-insoluble, the lightening ability of the bleach system decreases. The functional grouping of the surfactant appears to have little effect upon the efficiency of the resultant bleach mixture as long as water solubility is maintained.

The same is essentially true of those compositions that employ the other water-insoluble thickening agents mentioned above. These also require relatively high levels of ammonia to raise the activity of the bleach composition to a suitable level.

Applicants have found that by utilizing water-soluble surfactant thickening agents that it is possible to dispense with the need for using ammonia as an activator. In this case, a non-ammonia alkalizing agent and preferably one which does not have the potentiality for hair damage can be employed to give the composition its appropriate pH. However, when only water-soluble surfactant thickening agents are employed, the viscosity of the product when it is applied to the head is too low for satisfactory application of the bleach. When, on the other hand, an effort was made to increase the viscosity by the addition of water-insoluble surfactant thickening agents, it was found that the effectiveness of the bleaching composition i.e. the rate at which the bleaching action occured was reduced to an unacceptable level. However, if a small quantity of ammonia is present in the composition (no greater than 0.55% by weight based on the total weight of the composition measured as ammonium ion concentration) and the ratio of water-soluble to water-insoluble surfactant thickener was maintained in the range of from 1.8 to 7.0, a highly effective product is obtained having the requisite level of bleaching activity, a suitable viscosity in use for application of the bleach and substantially no ammonia odor.

It is accordingly an object of the present invention to provide hair bleaching compositions that are very low in ammonia concentrations giving substantially no ammonia odor, that is sufficiently active to give adequate bleaching with an acceptable level of hair damage and having a viscosity that is sufficiently high when applied to the hair on the head so that it does not run down the head.

It is also an object of the present invention to provide a multipart composition which when the parts are mixed provide compositions having the character set forth in the above object.

It is a further object of the present invention to provide a process for bleaching hair that employs the bleaching compositions set forth in the above objects.

Other and more detailed objects of this invention will be apparent from the following description and claims.

It is to be pointed out that percent (%) throughout the specification and claims is weight percent based on the total weight of the composition unless otherwise specified.

Efforts have been made in the prior art to provide ammonia free hair bleaching compositions. One such attempt is described in U.S. Pat. No. 2,283,350. This patent describes the use of aliphatic amines or alkanolamines in place of ammonia or ammonium hydroxide to get rid of the unpleasant ammonia odor. However, in this case, the resulting bleach mixture is more damaging (for the same degree of lightening) to the keratin hair fibers.

Another attempt at providing a non-ammonia hair bleach composition is described in the U.S. Pat. No. 3,816,615 to Zeffern et al. In this case, activation of the peroxide oxidizing agent is accomplished by means of certain dicarbonyl compounds. In place of ammonium hydroxide, the patentees employ certain guanidine salts. This invention has not received any wide acceptance in the industry which is probably due to the fact that the hair damage encountered in the use of the amines noted above is also encountered with the guanidine compounds which are expected to act in a manner similar to that of the other amines used in the prior art.

To obtain the necessary level of activity for the hydrogen peroxide solutions, it is necessary that the final bleaching composition have a pH of from about 9 to about 12 and preferably from about 9.7 to 10.3. Below a pH of 9, insufficient bleaching action occurs; whereas, above 12 an excessive amount of hair damage occurs.

To insure that the composition has the appropriate pH, an alkalizing agent and preferably one that is non-destructive to hair is employed. Useful alkalizing agents for this purpose include alkali metal meta-silicates such as sodium metasilicate; alkali metal carbonates, ortho-, meta- and tripolyphosphates, alkali metal silicates e.g. sodium silicate, etc.

It is generally well to avoid the use of amines, quaternary ammonium compounds, or alkanolamines in the compositions of the present invention because of their known destructive effect on hair. However, at very low levels of concentrations e.g. within the range of from 1.0% to 3.5% by weight they may be employed safely and even may serve as an activator for the hydrogen peroxide solution. Typically, these include amine or quaternary ammonium compounds selected from the group consisting of at least one of morpholine, mono-, di-, trialkanolamine, and mono-, di-, and trialkylamine, wherein the alkyl or alkanol substituents have a carbon chain length of 1 to 4 carbon atoms.

One of the chief purposes of the present invention is to provide a hair bleach composition that contains at most a minimal amount of ammonia as measured by the ammonium ion concentration. As mentioned above, when a water-soluble and water-insoluble surfactant gelling system is used, which system appears necessary to give the product a suitable viscosity when applied as a practical matter, it has been found necessary to employ a small quantity of ammonia to obtain the desired level of activity. The ammonia is present in the aqueous phase of the present composition and is measured as the ammonium ion concentration in the total composition. The ammonium ion concentration will be less than about 0.55% by weight based on the total weight of the composition and generally, in the range of from about 0.15% to about 0.55% by weight on the same weight basis.

Bleaching studies have surprisingly indicated that very good lightening, resulting in minimal hair damage, can be obtained with lotions containing an ammonium ion concentration of 0.55% by weight or less based on the total composition weight, while at the same time having a water phase that accounts for 80% to 100% by weight of the total composition. Studies have also indicated that hair lightening is not substantially affected by ammonia basicity i.e. the ammonia may nominally be present as either free $NH_3.H_2O$ or as the neuturalized ammonium ion $NH_4^+$. From a cosmetic viewpoint, the ammonium ion is preferable to free ammonia.

Because of the equilibrium between $NH_3$, $NH_3.H_2O$, $HN_4OH$, $NH_4^+$ and $OH^-$, it is not possible to have just one species present in an aqueous medium. The relative proportion of ammonia to ammonium can be shifted by pH, ionic strength, pressure and any other chemical technique that affects the concentration of each specie in the equilibrium constant. However, merely reducing amine or quaternary ammonium content, without also maintaining the higher concentrations of water-soluble components, or vice versa, as taught herein does not provide satisfactory hair lightening results. Moreover, to try to compensate for the inferior lightening resulting from using lower amine or quaternary ammonium concentrations by either using high concentrations of peroxygen compounds, alkaline ingredients, longer time periods for bleaching the hair, or higher temperature during the bleaching process will result in unsatisfactory damage levels to the hair. It is the intent of this invention to adjust the formula in such a way so as to favor the formation of ammonium ion and keep the concentration of free ammonia as close as practical to the value dictated by the equilibrium constant.

The resulting ammonium ion concentration in the present composition comes about from many factors not the least of which is the amount of ammonium compounds including ammonium precompounds present in the composition which are capable of ionizing in water to form the ammonium ion. Also affecting the ammonium ion concentration is the amount of other compounds that react with (e.g. neutralize) the ammonium ion, such as fatty acid compounds. Finally, there are factors associated with the equilibrium in solutions between the ammonium ion, ammonium hydroxide, and ammonia gas. Furthermore, it is observed that the use of amines in place of ammonium hydroxide will not result in the formation of ammonium ion, but requires greater amounts of the same because of lower efficiency compared to ammonium hydroxide.

It is also highly desirable to include in the bleach compositions of this invention at least one percompound. Generally, this can be used in a concentration range of from about 2% to about 20% by weight based on the total weight of the composition and preferably from about 6% to about 8% on the same weight basis. The percompound provides an additional source of oxygen generation necessary for bleaching, other than hydrogen peroxide. Such percompounds are not limited to but can be selected from the ammonium-, alkali metal- and alkaline earth metalperborates, persulfates, percarbonates, and carbonate peroxides. The term "alkali metal" and "alkaline earth metal" as used herein and throughout the specification are deemed to have their ordinary accepted meaning in the art.

It is also essential to have present hydrogen peroxide in a useful concentration range of about 1.5 to 7% to provide bleaching of the hair. Preferably, the hydrogen peroxide concentration is from about 3.2% to about 3.7%. Stabilizers for the hydrogen peroxide, such as phenacetin, may also be present in minor amounts.

As pointed out above, an essential component of the bleaching composition of the present invention is the use of water-soluble surfactant thickener. A variety of such water-soluble surfactant thickeners are known in the prior art which will serve these purposes. Of special interest are the water-soluble surfactant thickeners selected from the group consisting of:

(a) an alkylene glycol or an alkylene glycol ether alcohol of the formula:

$$R^5O(R^6O)_nR^7OH$$

wherein $R^5$ is H or alkyl having 1 to 4 carbon atoms and $R^6$ and $R^7$ are divalent alkylene radicals having 2 to 4 carbon atoms and n is a number from 0 to 150;

(b) a long chain fatty acid soap of the formula:

$$(R^8COO)_aM$$

wherein $R^8$ is the hydrocarbon moiety of a long chain fatty acid having 10 to 20 carbon atoms, M is a monovalent or polyvalent salt forming group and "a" is the valence of group M;

(c) a long chain polyoxyalkylated compound selected from the group consisting of a polyoxyalkylated long chain fatty alcohol, a polyoxyalkylated polyhydroxyalkyl ester of a long chain fatty acid; a polyoxyalkylated long chain amine; a polyoxyalkylated long chain fatty acid; a polyoxyalkylated long chain fatty acid amide; a polyoxyalkylated long chain alkylphenol and polyoxyalkylated laurate esters of sorbitol and its anhydrides containing about 8 to 300 oxyalkyl groups in the structure; and (d) mixtures thereof.

The quantity of water-soluble surfactant thickener that will be contained in the compositions of this invention will generally be in the range of from about 17% to about 27% by weight based on the total weight of the composition. One can employ such water-soluble surfactant thickeners as those described as "coupling agents" at column 5 line 29 to column 6, line 56 of U.S. Pat. No. 3,811,830 to R. DeMarco issued May 21, 1974, and incorporated by reference herein. Additionally, useful are ethoxylated laurate esters of sorbitol and its anhydrides such as with 80 moles ethylene oxide (Tween 80); acid ethoxylates such as di-stearic acid with 150 moles ethylene oxide (PEG 6000 Distearate); and block copolymers of ethylene oxide and propylene oxide (Pluronics). A preferred surfactant is cocoyl fatty acid ethoxylated with 8.5 moles of ethylene oxide.

Another essential ingredient of the present composition is the water-insoluble surfactant thickener. Included in the definition of these materials are those that are only slightly water-soluble. One or more of these surfactants may be included in the present compositions.

Typical of the water-insoluble surfactants that can be used for thickening properties are those well known in the art such as those disclosed in U.S. Pat. No. 3,811,830 to DeMarco at column 3, line 64 to column 5, line 6 which is incorporated by reference herein, called "oily materials". By way of further specific examples of the water-insoluble surfactant thickening agents that may be employed in the present invention, mention may be made of the following: polyethylene glycol (6 moles ethylene oxide) ether of tridecyl alcohol (Emulphogene BC 610); ethoxylated nonylphenol (4.0 moles ethylene oxide) (Igepal CO 430); cetyl alcohol; polyethylene glycol (5 moles ethylene oxide) ester of oleic acid (Emulphor UN 430); polyethylene glycol amine of soya acid (5.0 moles ethylene oxide) (Ethomene S-15); ethylhydroxymethyl oleyl oxazoline (Alkaterge E) and mixtures of the above.

It is pointed out that the use of natural gums (e.g. xanthum or guar gum) and cellulose-based thickening agents (e.g. carboxymethylcellulose derivatives) with or without solvents such as low molecular weight alcohols and ketones do not provide the necessary thickening properties for use herein. The gums and cellulose based agents being too difficult to conveniently mix and requiring excessive time to hydrate in order to build the necessary viscosity to maintain the bleaching composition on the hair. Solvents which generally couple oil-soluble materials and water-soluble surfactants produce compositions with low viscosity and are unsuitable for bleaching keratin fibers.

The quantity of water-insoluble surfactant thickener that will be contained in the compositions of the present invention may vary somewhat. However, generally it will comprise from about 4% to 13% by weight based on the total weight of the composition.

Water is another essential ingredient of the present composition. It provides the proper medium for the bleaching process to occur as previously discussed, and makes up the balance of the composition except for water-insoluble ingredients and other optional additives.

Among the optional additive ingredients are sequestering agents for complexing metal ion impurities which would tend to affect the stability of the hydrogen peroxide. Such sequestrants which may be present in a concentration up to about 0.5% and include the unneutralized and/or the alkali metal salts of nitrilotriacetic acid and alkylene polyamine polycarboxylic acids having the formula:

$$(HOOCCH_2)_2N[(CH_2)_xNCH_2COOH]_yCH_2COOH$$

wherein x and y may vary independently from 1 to 4. Representative of such acids are ethylenediaminetetraacetic acid and ethylenediaminetriacetic acid.

Also present may be up to about 1.5% of a viscosity modifier which can include water-soluble straight chain aliphatic alcohols (e.g. ethanol and butanol), aldehydes (e.g. acetaldehyde and butyraldehyde), ketones (e.g. acetone and 2-hexanone), and glycols (e.g. ethylene glycol and butylene glycol).

Additionally, the compositions can optionally include up to about 2% of additional water-insoluble ingredient which includes for example, perfumes, oils, water-insoluble fats, waxes, opacifiers and dyestuffs (including dyes and dispersible pigments).

Such dyestuffs include, for example, D&C Green #6, FD&C Yellow #3 and pigments like ultramine blue and disperse blue #1. Typical opacifiers include abietic/lauric ether polyesters, and polystyrene.

Oils include non-volatile oils such as mineral oil, isopropyl myristate, diisopropyl adipate, and volatile or essential oils such as peppermint, clove oil, and eucalyptus oils. The water-insoluble fats and waxes may be those derived from natural or synthetic sources (e.g. beeswax or spermaceti) and skin emollients well known in the art.

The various components constituting the present composition are mixed together to provide a thickened hair bleaching composition. The viscosity of this composition may vary somewhat. Ordinarily, this viscosity will fall in the range of about 5000 to 100,000 centipoises.

The compositions of the present invention are conveniently marketed as two or three part compositions in which the parts are maintained separately from each other until just before use although they may be packaged in the same carton. When the compositions are to be employed, the separated parts are mixed together and the resulting gelled product is applied to the head.

The three separate parts of the present compositions are identified as the lotion, activator and developer respectively. The principal components of lotion will usually be the surfactant gelling components although it may also contain the ammonium hydroxide or amine when these are added. The principal active component of the developer will be hydrogen peroxide although it may contain other components. The activator will usually contain the persalts and often will contain the non-hair damaging alkalizing agent (e.g. alkali metal silicate or metasilicate).

The product may be packaged for marketing as containing the lotion and activator maintained separately but packaged in the same carton. Here again, these will be maintained separately until just before use at which time all three parts are mixed together to form the gelled bleaching product that is applied to the head.

The following Examples are given to further illustrate the present invention. It is to be understood, however, that the invention is not limited thereto.

In the Examples that follow the test methods used for evaluating bleaching (i.e. hair lightening effectiveness) and alkaline solubility (i.e. hair damage) are described as follows:

Test Method for Evaluating Bleaching Effectiveness

Surfactants and their effect upon lightening and damage were evaluated as part of a three component system. The system contained a powdered activator, a lotion and a developer. The chemical composition of the activator and developer were kept constant with the lotion being the vehicle for the evaluation of the surfactant. The activator had the following composition:

| Ingredient | Grams | % by Wt. |
|---|---|---|
| ($Na_2Si_2O_5$) | 2.1 | 9.05 |
| Sodium lauryl sulfate | 0.5 | 2.15 |
| Methocel 60 HG (hydroxypropyl methyl cellulose) | 0.3 | 1.30 |
| Cabosil M5 (fumed silica dioxide) | 0.3 | 1.30 |
| Potassium persulfate | 10.0 | 43.10 |
| Sodium perrsulfate | 10.0 | 43.10 |
| | 23.2 | 100.00 |

The lotion consisted of 0.5% monoethanolamine (i.e. MEA) and 99.5% of the surfactant to be evaluated.

Bleaching tests were done as follows:

Twenty-three grams of activator were added to 4 oz. of a 6% aqueous hydrogen peroxide solution and shaken. Sixty grams of the test lotion was then added and shaken until thoroughly mixed. The pH and viscosity of the mixture were then measured. The mixture was spread over and through a swatch of brown pigmented hair. The swatch consisted of a blend of commercially available virgin hair approximately nine inches long. The bleaching was accomplished in a glass dish placed atop a constant temperature bath set at 38° C. The bleaching time was one hour with the swatch being turned over and the bleach mixture "reworked" every fifteen minutes. At the end of one hour, the bleach mixture was rinsed from the hair and the swatch shampooed with a mild shampoo. The swatch was then visually compared to a standard. If the swatches were comparable in lightening to the standard, the reflectance of each swatch was accurately measured at 560 mu on a Beckman DU-2 Spectrophotometer.

Where the surfactant was supplied as powdered solid material, the necessary MEA and solid surfactant are dissolved in the 6% hydrogen peroxide solution. The activator is then added to the resulting lotion/peroxide mixture and shaken until uniform. The bleaching process is the same as previously described.

Test Procedure—Alkaline Solubility Test

Bleach hair swatches at 38° C. for 1 hour in bleaching composition. Then dry 1 gram sample of bleached hair for 3 hours at 110° C. Weigh the dried hair sample. Then immerse hair for 1 hour in 100 ml of 0.1N sodium hydroxide at 66° C. Remove hair from sodium hydroxide solution and rinse with distilled water. Follow with rinse of 1% acetic acid solution. Again rinse with distilled water. Dry hair swatch for 3 hours at 110° C. Weigh sample and calculate weight loss. The greater the weight loss, the greater the hair damage that has occurred during the bleaching process.

The standard used was a commercially available Clairol Naturally Blonde Quick Lightening Kit comprising a three component system; 60 g of lotion; 120 g of developer and 28 g of activator (208 g total). Percent composition is as follows:

| Chemical Name | % by Wt. |
|---|---|
| Lotion | |
| Ammonium hydroxide (29% aq. solution) | 2.45 |
| Disodium ethylenediamine tetraacetic acid | 0.30 |
| Isopropanol | 3.75 |
| Ethoxydiglycol[1] | 1.01 |
| Ethoxylated nonylphenol (10 moles of ethylene oxide)[2] | 1.59 |
| Oleic acid | 10.10 |
| Polyethylene glycol ether of tridecyl alcohol (6 moles of ethylene oxide)[3]* | 1.20 |
| Ethylhydroxymethyl oleyl oxazoline[4] | 3.17 |
| Polyethylene glycol amine of soya acid (5 moles of ethylene oxide)[5] | 3.17 |
| Water | 2.22 |
| Fragrance | 0.14 |
| Developer | |
| Ethoxylated nonylphenol (4.0 moles of ethylene oxide)[6]* | 2.88 |
| Ethoxylated nonylphenol (9.0 moles of ethylene oxide)[7] | 2.88 |
| Cetyl alcohol* | 0.14 |
| Hydrogen peroxide (50% aq. solution) | 7.96 |
| Water | 44.68 |
| Activator | |
| Silica[8]* | 0.20 |
| Sodium metasilicate | 1.82 |
| Sodium lauryl sulfate | 0.16 |
| Disodium ethylenediamine tetraacetic acid | 0.16 |
| Ammonium persulfate | 2.80 |
| Potassium persulfate | 8.28 |

-continued

| Chemical Name | % by Wt. |
|---|---|
| | 100.00 |

[1] Trade Name: Carbitol PM 600
[2] Trade Name: Igepal DM 530
[3] Trade Name: Emulphogene BC 610
[4] Trade Name: Alkaterge C
[5] Trade Name: Varonic L 205
[6] Trade Name: Igepal CO 430
[7] Trade Name: Igepal CO 630
[8] Trade Name: Cabosil M5
Note
All of the oleic acid was converted to the water-soluble salt form This composition had an alkaline solubility of 30.2% (i.e. 30.2% of 1 g sample dissolved in alkaline solution). Ammonium ion concentration 1.70%; water-soluble phase 87.65%. In the Naturally Blonde composition and the examples that follow, the designation "*" indicates that the particular ingredient is not water-soluble or only slightly water-soluble. Also, the wt. % of the water-soluble phase is determined by subtracting from 100% the wt. % of insoluble ingredients.

Additionally, the maximum ammonium ion concentration in the composition is determined by assuming complete ionization of the ammonium percompound and ammonium hydroxide.

In accordance with the aforementioned Bleaching and Alkaline Solubility Test methods, bleaching compositions including the following water-soluble surfactant thickeners tested and gave comparable and satisfactory light reflectance and alkaline solubility levels as that for Naturally Blonde:

| Chemical Class | Trade Name |
|---|---|
| Ethoxylated primary fatty amine | Ethomeen C/25 |
| Ethoxylated fatty acids | Ethofat 242/25 |
| Ethoxylated dialkyl quaternary ammonium salts | Ethoquad 18/25 |
| Ethoxylated fatty alcohols | Brij ® 35 |
| Propoxylated fatty alcohols | Procetyl ® 50 |
| Ethoxylated lanolin | Solulan 75 |
| Ethoxylated lanolin alcohols | Solulan 25 |
| Acetylated polyoxyethylene lanolin derivatives | Solulan 97 |
| Nonylphenoxypoly(ethyleneoxy) types | Igepal CO 630 |
| Polyethylene/propylene glycols | Pluronics/Carbowaxes |
| Polyethylene glycol 1000 monostearate | Collemol 510 |

In the Examples 1 through 5 that follow, the resulting bleaching compositions had a pH of 9.8–10 and were evaluated using the aforementioned test methods for bleaching and alkaline solubility, except where indicated otherwise, providing similar light reflectance and solubility levels to that for Naturally Blonde.

EXAMPLE 1

Three component system, 66 g of lotion, 120 g of developer and 28 g of activator (214 g total) were mixed as previously described. Percent composition is as follows:

| Chemical Name | % by Wt. |
|---|---|
| Lotion | |
| Laurate esters of sorbitol and sorbitol anhydrides condensed with 80 moles of ethylene oxide[1] | 23.26 |
| Polyethylene glycol ester of oleic acid (5 moles of ethylene oxide)[2]* | 4.67 |
| Monoethanolamine | 2.80 |
| Developer | |
| Hydrogen peroxide (50% aq. solution) | 6.89 |
| Water | 49.18 |
| Activator | |
| Potassium persulfate | 2.95 |
| Ammonium persulfate | 0.92 |
| Sodium persulfate | 2.95 |
| Disodium ethylenediamine tetraacetic acid | 0.13 |
| Sodium metasilicate | 6.15 |
| | 100.00 |
| Water soluble phase 95.33% | |
| Ammonium ion concentration 0.15% | |

[1] Trade Name: Tween 80
[2] Trade Name: Emulphor VN-430

EXAMPLE 2

Three component system, 60 g of lotion; 120 g of developer and 28 g of activator (208 g total) were mixed as previously described. Percent composition is as follows:

| Chemical Name | % by Wt. |
|---|---|
| Lotion | |
| Oleic acid | 6.34 |
| Ethoxylated cocoyl fatty acid (8.5 moles of ethylene oxide)[1] | 9.23 |
| Ethoxylated nonylphenol (4.0 moles of ethylene oxide)[2]* | 3.10 |
| Polyethylene glycol amine of soya acid (5.0 moles of ethylene oxide)[3]* | 2.88 |
| Ethanol | 1.55 |
| Polypropylene glycol ether of cetyl alcohol (50 moles of ethylene oxide)[4] | 5.77 |
| Perfume | 0.08 |
| Ammonium hydroxide (29% aq. solution) | 0.29 |
| Developer | |
| Hydrogen peroxide (50% aq. solution) | 7.10 |
| Water | 50.20 |
| Activator | |
| Potassium persulfate | 3.03 |
| Ammonium persulfate | 0.94 |
| Sodium persulfate | 3.03 |
| Disodium methylenediamine tetraacetic acid | 0.13 |
| Sodium metasilicate | 6.33 |
| | 100.00 |
| Water soluble phase 94.02% | |
| Ammonium ion concentration 0.24% | |

[1] Trade Name: Nu-Mole 7A-CM
[2] Trade Name: Igepal CO-430
[3] Trade Name: Ethomeen S-15
[4] Trade Name: Procetyl 50

EXAMPLE 3

Two component system; 88 g of activator is mixed with 120 g of developer (208 g total). Percent composition is as follows:

| Chemical Name | % by Wt. |
|---|---|
| Activator | |

-continued

| Chemical Name | % by Wt. |
|---|---|
| Ethoxylated nonylphenol (150 moles of ethylene oxide)[1] | 12.79 |
| Polyethylene glycol diester of stearic acid (150 moles of ethylene oxide)[2] | 0.78 |
| Palmitic acid[3] | 2.19 |
| Disodium methylenediamine tetraacetic acid | 0.26 |
| Sodium metasilicate | 11.75 |
| Sodium persulfate | 5.88 |
| Potassium persulfate | 5.88 |
| Ammonium persulfate | 2.78 |
| Developer | |
| Ethoxylated nonylphenol (4.0 moles of ethylene oxide)[4]* | 2.89 |
| Ethoxylated nonylphenol (9.0 moles of ethylene oxide)[5] | 2.89 |
| Cetyl alcohol* | 0.14 |
| Hydrogen peroxide (50% aq. solution) | 7.09 |
| Water | 44.68 |
| | 100.00 |

Water-soluble phase 96.97%
Ammonium ion concentration 0.440%

[1]Trade Name: Igepal DM 970
[2]Trade Name: PEG 6000 distearate
[3]Trade Name: Neo-Pat 16
[4]Trade Name: Igepal CO 430
[5]Trade Name: Igepal CO 630

EXAMPLE 4

Three component system; 60 g of lotion, 120 g of developer and 28 g of activator (208 g total) were mixed as previously described. Percent composition is as follows:

| Chemical Name | % by Wt. |
|---|---|
| Lotion | |
| Oleic acid | 7.21 |
| Ethoxylated cocyl fatty acid (8.5 moles of ethylene oxide)[1] | 6.35 |
| Ethoxylated nonylphenol (4.0 moles of ethylene oxide)[2]* | 2.02 |
| Ethylhydroxymethyl oleyl oxazoline[3]* | 3.97 |
| Polyethylene glycol amine of soya acid (5.0 moles of ethylene oxide)[4]* | 2.88 |
| Ammonium hydroxide (29% aq. solution) | 0.29 |
| Ethanol | 1.15 |
| Polypropylene glycol ether of cetyl alcohol (5.0 moles of ethylene oxide)[5] | 4.90 |
| Fragrance | 0.07 |
| Developer | |
| Hydrogen peroxide (50% aq. solution) | 7.10 |
| Water | 44.70 |
| Cetyl alcohol* | 0.14 |
| Ethoxylated nonylphenol (4 moles of ethylene oxide)[2]* | 2.88 |
| Ethoxylated nonylphenol (9 moles of ethylene oxide)[6] | 2.88 |
| Activator | |
| Potassium persulfate | 3.03 |
| Ammonium persulfate | 0.94 |
| Sodium persulfate | 3.03 |
| Disodium methylenediamine tetraacetic acid | 0.13 |
| Sodium metasilicate | 6.33 |
| | 100.00 |

Water-soluble phase 88.11%
Ammonium ion concentration 0.24%

-continued

| Chemical Name | % by Wt. |
|---|---|
| Alkaline solubility 30.7% | |

[1]Trade Name: Nu-Mole CM-7A
[2]Trada Name: Igepal CO-430
[3]Trade Name: Alkaterge E
[4]Trade Name: Ethomeen S-15
[5]Trade Name: Procetyl 50
[6]Trade Name: Igepal CO-630

EXAMPLE 5

| Chemical Name | % by Wt. | Wt. % Total Comp. |
|---|---|---|
| Lotion | | |
| Tall oil fatty acid[1] | 25.00 | 7.21 |
| Ethoxylated cocoyl fatty acid (8.5 moles ethylene oxide)[2] | 22.00 | 6.34 |
| Ethoxylated nonyl phenol (4.0 moles ethylene oxide)[3] | 7.00 | 2.02 |
| Ethyl hydroxymethyl oleyl oxazoline[4] | 13.70 | 3.95 |
| Polyoxyethylene soya amine (5 moles ethylene oxide)[5] | 10.00 | 2.88 |
| Ammonium hydroxide (29% aq.) | 1.00 | 0.29 |
| Ethanol | 4.00 | 1.15 |
| Polyoxypropylene cetyl alcohol (50 moles ethylene oxide)[6] | 17.00 | 4.90 |
| Fragrance | 0.30 | 0.09 |
| | 100.00 | |

Water-soluble phase 21.29% total comp.
Ammonium ion concentration .24%

| Activator | | |
|---|---|---|
| Disodium ETDA | 1.0 | 0.13 |
| GD Silicate (sodium silicate) | 47.0 | 6.33 |
| Sodium persulfate | 22.5 | 3.03 |
| Potassium persulfate | 22.5 | 3.03 |
| Ammonium persulfate | 7.0 | 0.94 |
| | 100.00 | |
| Developer | | |
| Ethoxylated nonylphenol (4.0 moles of ethylene oxide)[6]* | 4.92 | 2.84 |
| Ethoxylated nonylphenol (9.0 moles of ethylene oxide)[7] | 4.92 | 2.84 |
| Cetyl alcohol* | .24 | 0.14 |
| Hydrogen peroxide (50% aqueous solution) | 13.60 | 7.85 |
| Water | 76.32 | 44.04 |
| | 100.00 | |

[1]Tall oil fatty acids as used herein refers to the commercial product "Acintol EPG" and is a mixture of fatty acids having the following average composition: palmitic acid (0.5%), palmitoleic acid (0.5%), stearic acid (2.5%), oleic acid (52.5%), linoleic acid (37.0%), linoleic acid conjugated (as determined by UV and containing higher molecular weight polyunsaturated fatty acids) (6%), other miscellaneous acids and unknowns 1%.
[2]Trade Name: Nu-Mole CM-7A
[3]Trade Name: Igepal CO 430
[4]Trade Name: Alkaterge E
[5]Trade Name: Ethomeen S-15
[6]Trade Name: Procetyl 50

A three component system is prepared from the above lotion, developer and activator by mixing these components in the following amounts: 60 g of lotion, 120 g of developer and 28 g of activator.

What is claimed is:

1. An aqueous thickened low ammonia hair bleaching composition comprising based on the total composition:
   (a) from about 1.5% to about 7% by weight of hydrogen peroxide;

(b) from about 17% to about 27% by weight of at least one water-soluble surfactant thickener selected from the group consisting of
  (i) an alkylene glycol or an alkylene glycol ether alcohol of the formula:

$R^5O(R^6O)_nR^7OH$ wherein $R^5$ is H or alkyl having 1 to 4 carbon atoms and $R^6$ and $R^7$ are divalent alkylene radicals having 2 to 4 carbon atoms and n is a number from 1 to 150;
  (ii) a long chain fatty acid soap of the formula:

$(R^8COO)_aM$ wherein $R^8$ is the hydrocarbon moiety of a long chain fatty acid having 10 to 20 carbon atoms, M is a monovalent or polyvalent salt-forming group and "a" is the valence of group M;
  (iii) a long chain polyoxyalkylated compound selected from the group consisting of a polyoxyalkylated long chain fatty alcohol, a polyoxyalkylated polyhydroxyalkyl ester of a long chain fatty acid; a polyoxyalkylated long chain fatty acid; a polyoxyalkylated long chain fatty acid amide; a polyoxyalkylated long chain alkylphenol and polyoxyalkylated laurate esters of sorbitol and its anhydrides containing about 8 to 300 oxyalkyl groups in the structure; and
  (iv) mixtures thereof;
(c) from about 4% to about 13% by weight of a water-insoluble surfactant thickener selected from the group consisting of polyethylene glycol (6 moles ethylene oxide) ether of tridecyl alcohol; ethoxylated nonylphenol (4.0 moles of ethylene oxide); cetyl alcohol; polyethylene glycol (5 moles ethylene oxide) ester of oleic acid; polyethylene glycol amine of soya acid (5.0 moles ethylene oxide); ethylhydroxymethyl oleyl oxazoline and mixtures of the above;
(d) sufficient non-hair damaging alkalizing agent to give the composition a pH of from about 9 to 12 and selected from the group consisting of alkali metal metasilicates; alkali metal carbonates; ortho-, meta and tri-polyphosphates and alkali metal silicates;
(e) from about 2% to about 20% by weight of at least one percompound selected from the group consisting of an ammonium-, alkali metal- and alkaline earth metaperborate, persulfate, percarbonate, and carbonate peroxide;
(f) wherein the ammonium ion concentration is in the range of from about 0.15% to about 0.55% by weight whereby only trace amounts of ammonia gas are produced as a result of interaction of these ingredients with each other or with hair; and
(g) wherein the ratio of water-soluble surfactant thickener to water-insoluble surfactant thickener is in the range of from about 1.8 to about 7.0;
(h) said composition being very low in ammonia concentration giving substantially no ammonia odor but being sufficiently active to give adequate bleaching with an acceptable level of hair damage, said composition also having a viscosity sufficiently high when applied to the hair on the head so that it does not run down the head.

2. The composition of claim 1 additionally containing up to about 0.5% by weight of a sequestering agent.

3. The composition of claim 1 additionally containing up to about 1.5% by weight of a viscosity modifier selected from the group consisting of a water-soluble straight chain aliphatic alcohol, aldehyde, ketone, glycol, and mixtures thereof, having a carbon chain length of 1 to 6 carbon atoms.

4. The composition of claim 1 additionally containing up to about 2% of at least one additional water-insoluble ingredient selected from the group consisting of perfumes, oils, opacifiers, dyestuffs and mixtures thereof.

5. The composition of claim 1 wherein said percompound weight percent is about 6 to about 8.

6. The composition of claim 5 wherein said hydrogen peroxide weight percent is about 3.2 to about 3.7.

7. The composition of claim 6 wherein said pH is about 9.7 to about 10.3.

8. The composition of claim 7 wherein said water-soluble surfactant thickener is cocoyl fatty acid ethoxylated with 8.5 moles of ethylene oxide.

9. As an article of manufacture a container containing a lotion component, an activator component and a developer component, each of said components being packaged separately in said container and adapted to be mixed with each other just before use to give an aqueous thickened low ammonia hair bleaching composition comprising based on the total composition:
(a) from about 1.5% to about 7% by weight of hydrogen peroxide;
(b) from about 17% to about 27% by weight of at least one water-soluble surfactant thickener selected from the group consisting of
  (i) an alkylene gylcol or an alkylene glycol ether alcohol of the formula:

$R^5O(R^6O)_nR^7OH$ wherein $R^5$ is H or alkyl having 1 to 4 carbon atoms and $R^6$ and $R^7$ are divalent alkylene radicals having 2 to 4 carbon atoms and n is a number from 1 to 150;
  (ii) a long chain fatty acid soap of the formula:

$(R^8COO)_aM$ wherein $R^8$ is the hydrocarbon moiety of a long chain fatty acid having 10 to 20 carbon atoms, M is a monovalent or polyvalent salt-forming group and "a" is the valence of group M;
  (iii) a long chain polyoxyalkylated compound selected from the group consisting of a polyoxyalkylated long chain fatty alcohol, a polyoxyalkylated polyhydroxyalkyl ester of a long chain fatty acid; a polyoxyalkylated long chain fatty acid; a polyoxyalkylated long chain fatty acid amide; a polyoxyalkylated long chain alkylphenol and polyoxyalkylated laurate esters of sorbitol and its anhydrides containing about 8 to 300 oxyalkyl groups in the structure; and
  (iv) mixtures thereof;
(c) from about 4% to about 13% by weight of a water-insoluble surfactant thickener selected from the group consisting of polyethylene glycol (6 moles ethylene oxide) ether of tridecyl alcohol; ethoxylated nonylphenol (4.0 moles of ethylene oxide); cetyl alcohol; polyethylene glycol (5 moles ethylene oxide) ester of oleic acid; polyethylene glycol amine of soya acid (5.0 moles ethylene oxide); ethylhydroxymethyl oleyl oxazoline and mixtures of the above;

(d) sufficient non-hair damaging alkalizing agent to give the composition a pH of from about 9 to 12 and selected from the group consisting of alkali metal metasilicates; alkali metal carbonates; ortho-, meta and tri-polyphosphates and alkali metal silicates;

(e) from about 2% to about 20% by weight of at least one percompound selected from the group consisting of an ammonium-, alkali metal- and alkaline earth metaperborate, persulfate, percarbonate, and carbonate peroxide;

(f) wherein the ammonium ion concentration is in the range of from about 0.15% to about 0.55% by weight whereby only trace amounts of ammonia gas are produced as a result of interaction of these ingredients with each other or with hair; and (g) wherein the ratio of water-soluble surfactant thickener to water-insoluble surfactant thickener being in the range of from about 1.8 to about 7.0;

(h) said composition being very low in ammonia concentration giving substantially no ammonia odor but being sufficiently active to give adequate bleaching with an acceptable level of hair damage, said composition also having a viscosity sufficiently high when applied to the hair on the head so that it does not run down the head.

10. The composition of claim 9 additionally containing up to about 0.5% by weight of a sequestering agent.

11. The composition of claim 9 additionally containing up to about 1.5% by weight of a viscosity modifier selected from the group consisting of a water-soluble straight chain aliphatic alcohol, aldehyde, ketone, glycol and mixtures thereof, having a carbon chain length of 1 to 6 carbon atoms.

12. The composition of claim 9 additionally containing up to about 2% of at least one additional water-insoluble ingredient selected from the group consisting of perfumes, oils, opacifiers, dyestuffs and mixtures thereof.

13. The composition of claim 9 wherein said percompound weight percent is about 6 to about 8.

14. The composition of claim 13 wherein said hydrogen peroxide weight percent is about 3.2 to about 3.7.

15. The composition of claim 14 wherein said pH is about 9.7 to about 10.3.

16. The composition of claim 15 wherein said water-soluble surfactant thickener is cocoyl fatty acid ethoxylated with 8.5 moles of ethylene oxide.

17. A process for bleaching hair which comprises applying to said hair the composition of claims 1, 9, 2, 3, 4, 5, 6, 7, 8, 10, 11, 12, 13, 14, 15 or 16 for time sufficient to bleach said hair and then removing said composition from said hair.

* * * * *